United States Patent
Fisher et al.

(10) Patent No.: US 7,653,769 B2
(45) Date of Patent: Jan. 26, 2010

(54) MANAGEMENT OF DEVICES CONNECTED TO INFINIBAND PORTS

(75) Inventors: Mark Edward Fisher, Rochester, MN (US); Charles Scott Graham, Rochester, MN (US); Thomas Rembert Sand, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 354 days.

(21) Appl. No.: 11/610,634

(22) Filed: Dec. 14, 2006

(65) Prior Publication Data

US 2008/0144531 A1    Jun. 19, 2008

(51) Int. Cl.
*G06F 13/00*    (2006.01)
(52) U.S. Cl. .......................... 710/104; 710/16; 710/63
(58) Field of Classification Search ......... 710/300–317, 710/104–105, 8–19, 62–64, 15–17; 709/223
See application file for complete search history.

(56) References Cited

U.S. PATENT DOCUMENTS

| | | | |
|---|---|---|---|
| 6,735,660 B1 * | 5/2004 | Osten et al. | 710/305 |
| 6,988,161 B2 * | 1/2006 | McConnell et al. | 710/316 |
| 7,111,101 B1 * | 9/2006 | Bourke et al. | 710/305 |
| 7,210,056 B2 * | 4/2007 | Sandven et al. | 713/600 |
| 7,421,488 B2 * | 9/2008 | Elko et al. | 709/223 |
| 2003/0018761 A1 * | 1/2003 | Doyle et al. | 709/223 |

* cited by examiner

*Primary Examiner*—Raymond N Phan
(74) *Attorney, Agent, or Firm*—Patterson & Sheridan, LLP

(57) ABSTRACT

Methods and systems for discovering and managing devices connected to InfiniBand ports are provided. The discovery may be performed by an end node, such that the end node interoperates with all standard InfiniBand components. Specific actions that are vendor unique, and potentially not compliant with the InfiniBand architecture, may not be done until after the discovery is complete and it has been verified that the noncompliant action will only be directed to entities known to be capable of processing them. These actions may include assuming the configuration responsibilities that would have been performed by the Subnet Manager in a standard InfiniBand network.

20 Claims, 12 Drawing Sheets

US 7,653,769 B2

MANAGEMENT OF DEVICES CONNECTED TO INFINIBAND PORTS

CROSS-REFERENCE TO RELATED APPLICATION

This application is related to commonly assigned U.S. application Ser. No. 11/610,638, filed herewith.

BACKGROUND OF THE INVENTION

1. Field of the Invention

The present invention generally relates to InfiniBand port monitoring. More specifically, the invention relates to determining the type of node connected to an InfiniBand port and identifying proprietary devices attached to an InfiniBand port.

2. Description of the Related Art

InfiniBand is an industry standard architecture that may be used for interconnecting systems in cluster configurations, by providing a channel-based, switched-fabric technology. In such a configuration, data may be transmitted via messages which are made up of packets. Each device, whether processor or I/O, may include a channel adapter. The messages are typically transmitted from one device's channel adapter to another device's channel adapter via switches. The InfiniBand architecture is described in "InfiniBand Architecture Specification Vol. 1-2." October 2004, Release 1.2, which is herein incorporated by reference in its entirety.

An InfiniBand network may also include a number of management entities such as Subnet Managers (SM) and Subnet Management Agents (SMA). Typically, the Subnet Managers are responsible for configuration of the network and for handling the dynamic addition and removal of nodes from the network. The InfiniBand architecture may be implemented in numerous configurations, including replacing the current generation of proprietary high speed interconnects used by many server manufacturers.

For many configurations, the cost associated with the Subnet Managers, and a large number of switches, becomes significant. One possible way to reduce this cost is to connect proprietary devices directly to an InfiniBand port. These proprietary devices typically do not require switches or a Subnet Manager. On other InfiniBand ports there may still be a standard InfiniBand network. However without a Subnet Manager, difficulties may arise when attempting to configure and manage the proprietary devices. There may also be problems maintaining compatibility with the InfiniBand protocols required for the InfiniBand port to operate properly. The absence of a Subnet Manager may also cause difficulties preventing interoperability problems with ports that do connect to a standard InfiniBand Network.

Therefore, what is needed is the ability to identify and manage multiple InfiniBand links in a mixed environment with switches and proprietary devices.

SUMMARY OF THE INVENTION

Embodiments of the present invention generally provide methods and apparatus to identify and manage multiple InfiniBand links in a mixed environment with switches and proprietary devices.

One embodiment of the present invention provides a method of managing one or more devices connected to one or more InfiniBand ports. The method generally includes detecting a change in physical state of one of the ports indicating a presence of a device and, in response to detecting the change in physical state, performing discovery operations to determine the type of the present device, wherein the discovery operations include determining whether the device is a proprietary device that is at least partially InfiniBand non-compliant, and communicating with the device using an appropriate protocol for the determined type.

One embodiment of the present invention provides a computer-readable medium containing a program for managing an InfiniBand port. When executed, the program performs operations generally including detecting a change in physical state of one of the ports indicating a presence of a device and in response to detecting the change in physical state, performing discovery operations to determine the type of the present device, wherein the discovery operations include determining whether the device is a proprietary device that is at least partially InfiniBand non-compliant, and communicating with the device using an appropriate protocol for the determined type.

One embodiment of the present invention provides an apparatus generally including one or more InfiniBand ports and a port connection manager. The port connection manager is generally configured to detect a change in physical state of the port indicating a presence of the device and in response to detecting the change in physical state, perform discovery operations to determine the type of the present device, wherein the discovery operations include determining whether the device is a proprietary device that is at least partially InfiniBand non-compliant, and communicating with the device using an appropriate protocol for the determined type.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention provide methods and systems for discovering whether a given connection to an InfiniBand port is a standard InfiniBand connection or a non-standard connection (e.g., indicating the presence of a proprietary device). The discovery may be performed by an end node, such that the end node interoperates with all standard InfiniBand components. Specific actions that are vendor unique, and potentially not compliant with the InfiniBand architecture, may not be done until after the discovery is complete and it has been verified that the noncompliant action will only be directed to entities know to be capable of processing them. These actions may include assuming the configuration responsibilities that would have been performed by the Subnet Manager in a standard InfiniBand network.

The techniques described herein may be utilized to manage systems having multiple InfiniBand ports with InfiniBand compliant devices, InfiniBand non-compliant devices, or a combination of both, connected to the ports. Devices (such as proprietary devices) may be InfiniBand non-compliant in a number of ways. As an example, a device may not be electrically InfiniBand compliant, but it may also not be compliant in other ways too. As an alternative, or in addition, the protocol used to communicate with the device may be InfiniBand non-compliant (either partially so the device only responds to a very limited set of InfiniBand compliant requests, or in whole so the device doesn't respond to any InfiniBand compliant requests). In any cases, the discovery and management techniques described herein may be used to discover and/or manage different types of InfiniBand non-compliant devices.

In the following, reference is made to embodiments of the invention. However, it should be understood that the invention is not limited to specific described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

An Exemplary InfiniBand Network

Figure 1:
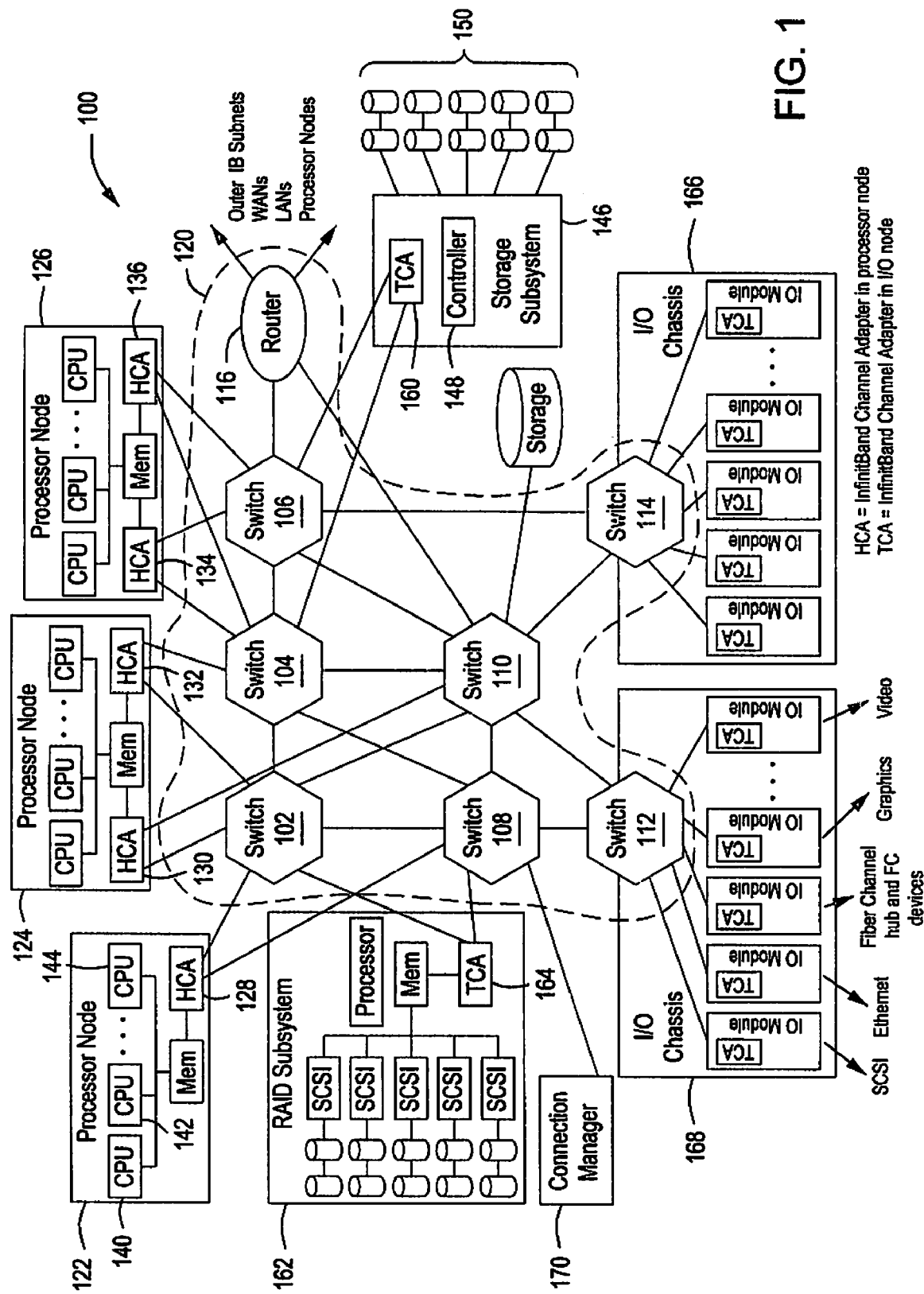
FIG. 1 is an illustration of an exemplary InfiniBand network containing a connection manager according to an embodiment of the invention.

InfiniBand implementations may be found in servers, server clusters, embedded computing systems and in both block and file based storage systems. FIG. 1 illustrates an exemplary InfiniBand implementation 100. Switches 102-114 and a router 116 form the subnet 120. Multiple processor nodes 122-126 may be connected to switches within the subnet 120 through InfiniBand channel adapters 128-136. As illustrated by processor Node 122, a processor node may contain multiple CPUs 140-144 and may have a single InfiniBand channel adapter 128. As depicted, the channel adapter 128 may be connected to both switch 102 and switch 108. As illustrated by processor node 124, a processor node may contain more than one channel adapter 130 and 132 connected to different switches 102 and 104.

Each channel adapter 128-136 may have a globally unique identifier (GUID) that is assigned by the channel adapter vendor. Local identification numbers assigned by the subnet manager may not be persistent (i.e., they may change from one power cycle to the next,) the channel adapter globally unique identifier may become the primary object used for persistent identification of a channel adapter. Additionally, each port may have a port GUID assigned by the manufacturer. Every destination within a subnet may also be configured with one or more unique local identifiers (LIDs). Packets may contain a destination address that specifies the LID of the destination. From the point of view of a switch, a destination LID may represent a path through the switch. Switches 102-114 may be configured with forwarding tables and an individual packet may be forwarded to an output port based on the packet's destination LID and the switch's forwarding table.

Switches 102-114 may primarily pass packets along based on a destination address within the packet's local route header. Switches 102-114 may also consume packets required for managing the switches 102-114 themselves. Optionally, a switch port may incorporate the properties of a physical InfiniBand channel adapter. Switches 102-114 may also support delivery of a single packet to a single destination as well as the delivery of a single packet to multiple destinations.

Various types of storage devices may also be connected to switches within the subnet 120. A storage subsystem 146 containing a storage capacity 150, a controller 148 and an InfiniBand channel adapter 160 may be connected to switches 104 and 106. A RAID storage subsystem 162 may also be connected via InfiniBand channel adapter 164 to switches 108 and 102 within the subnet 120. As well as the storage subsystems 146 and 162, I/O chassis 166 and 168 may be connected to switches 112 and 114 respectively. In addition, a connection manager 170 may be connected to switch 108 within the subnet 120. While the connection manager 170 is independently depicted, in some embodiments it may be contained within a server, a console, a processor node, a storage subsystem, an I/O chassis or in another device connected to the subnet 120.

An Exemplary Connection Manager

Figure 2:
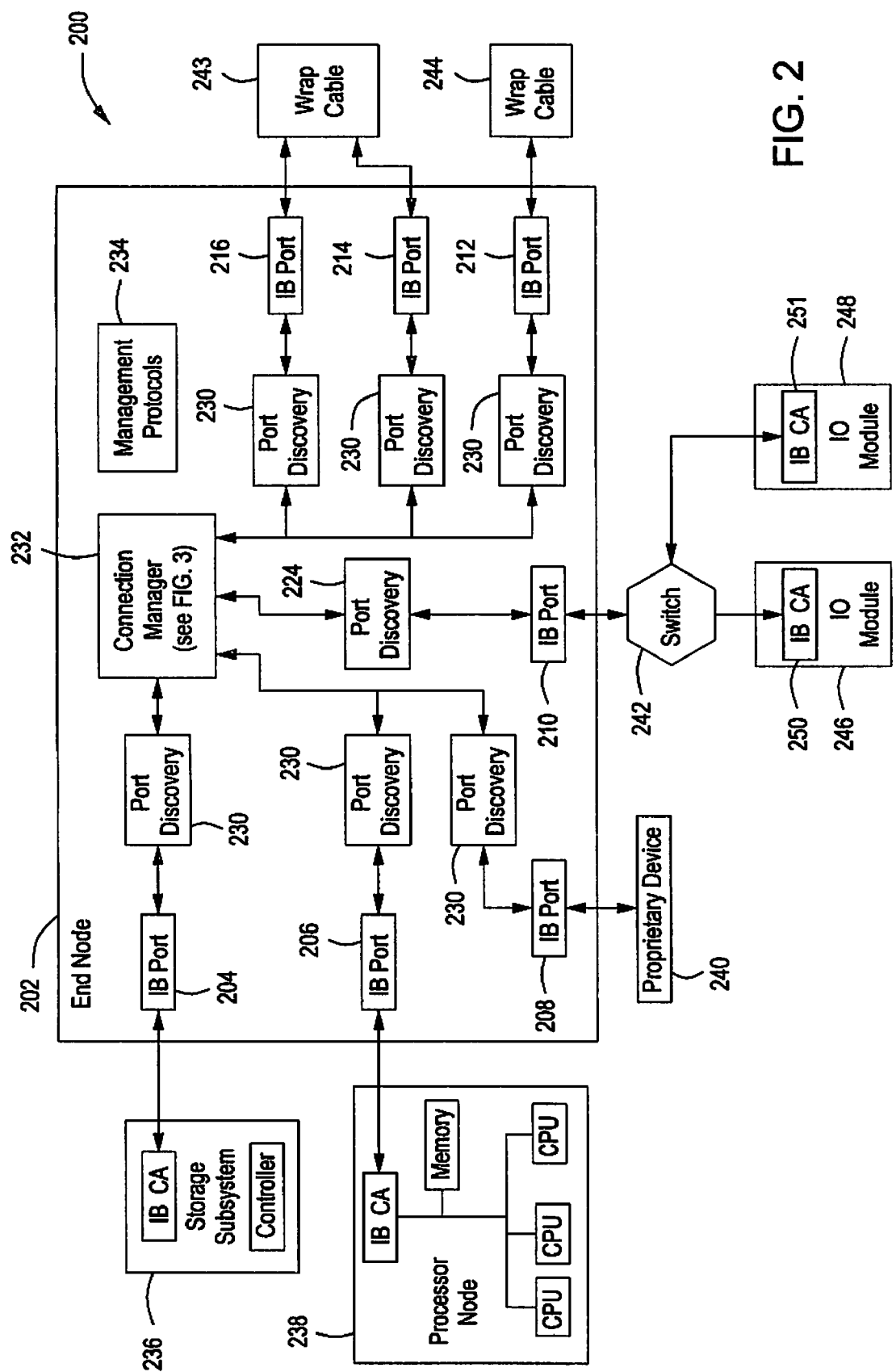
FIG. 2 is an illustration of an exemplary connection manager according to an embodiment of the invention.

A connection manager 232 may contain, and control, one or more InfiniBand ports. FIG. 2 illustrates a system 200 utilizing one exemplary implementation of an end node 202 may contain InfiniBand ports 204-216, port discovery logic 230 for each InfiniBand port, a connection manager 232, and management protocol definitions 234. The management protocols 234 may comprise proprietary protocols necessary to detect and control proprietary devices as well as InfiniBand protocols necessary for InfiniBand compliant devices.

A variety of different type devices may be connected to the InfiniBand ports 204-216. As illustrated, these devices may include a storage subsystem 236, a processor node 238, a proprietary device 240, a switch 242, a wrap plug 244 and a wrap cable 243. Switch 242 may also be connected to I/O modules 246 and 248 via InfiniBand channel adapters 250 and 251, respectively.

The InfiniBand ports 204-216 may be in a number of physical states, including LinkDown, Sleep, Polling, Disabled, Port Configuration Training, LinkUp, LinkErrorRecovery and Physical Test. The physical state of an InfiniBand port may be represented by PortPhysicalState. PortPhysicalState is an architected state that reflects whether an InfiniBand port is physically connected to the subnet. The LinkUp state represents an "electrically connected" state and all other states represent an "electrically disconnected or connecting" state, LinkDown. A LinkUp state typically indicates the port is available to transmit packets, while a LinkDown state typically indicates the port is not available to transmit packets. In order to identify a device connected to a port, the port discovery logic 230 for that port may monitor that port for a change in physical state.

Figure 3:
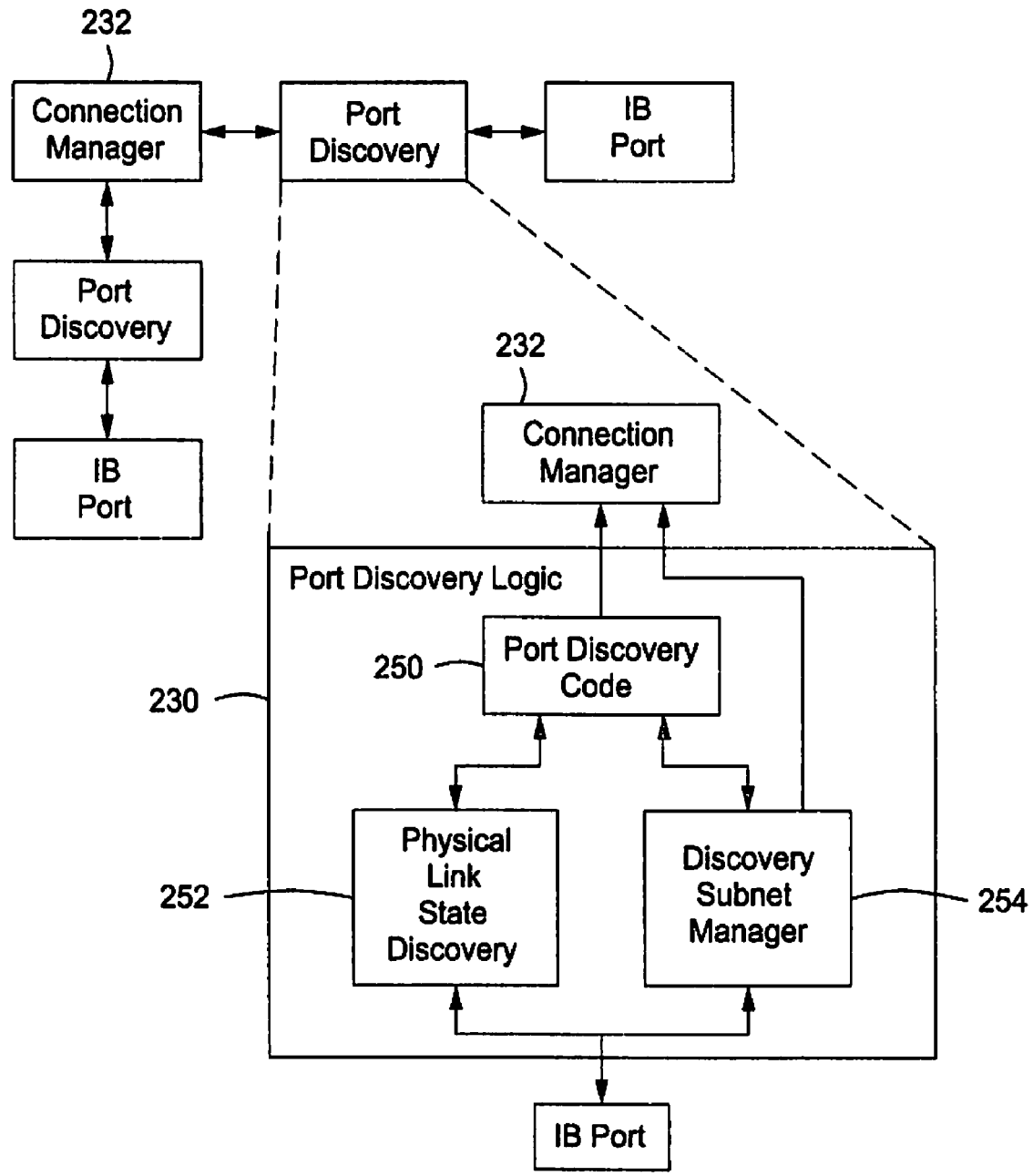
FIG. 3 is a logical diagram of exemplary components of port discovery logic shown in FIG. 2.

As illustrated in FIG. 3, for some embodiments, the port discovery logic 230 may include controlling PortDiscovery code 250 (e.g., a set of firmware instructions), physical link state discovery logic 252, and a discovery subnet manager (DSM) 254. Through communications with the physical link state discovery logic 252, the PortDiscovery code 250 may discover a device connected to the corresponding port and bring the port state to a LinkUp state, when appropriate. As illustrated, the PortDiscovery code 250 and DSM 254 may communicate with connection manager 232, while the physical link state discovery logic 252 and DSM 254 may communicate with the physical port.

Figure 4:
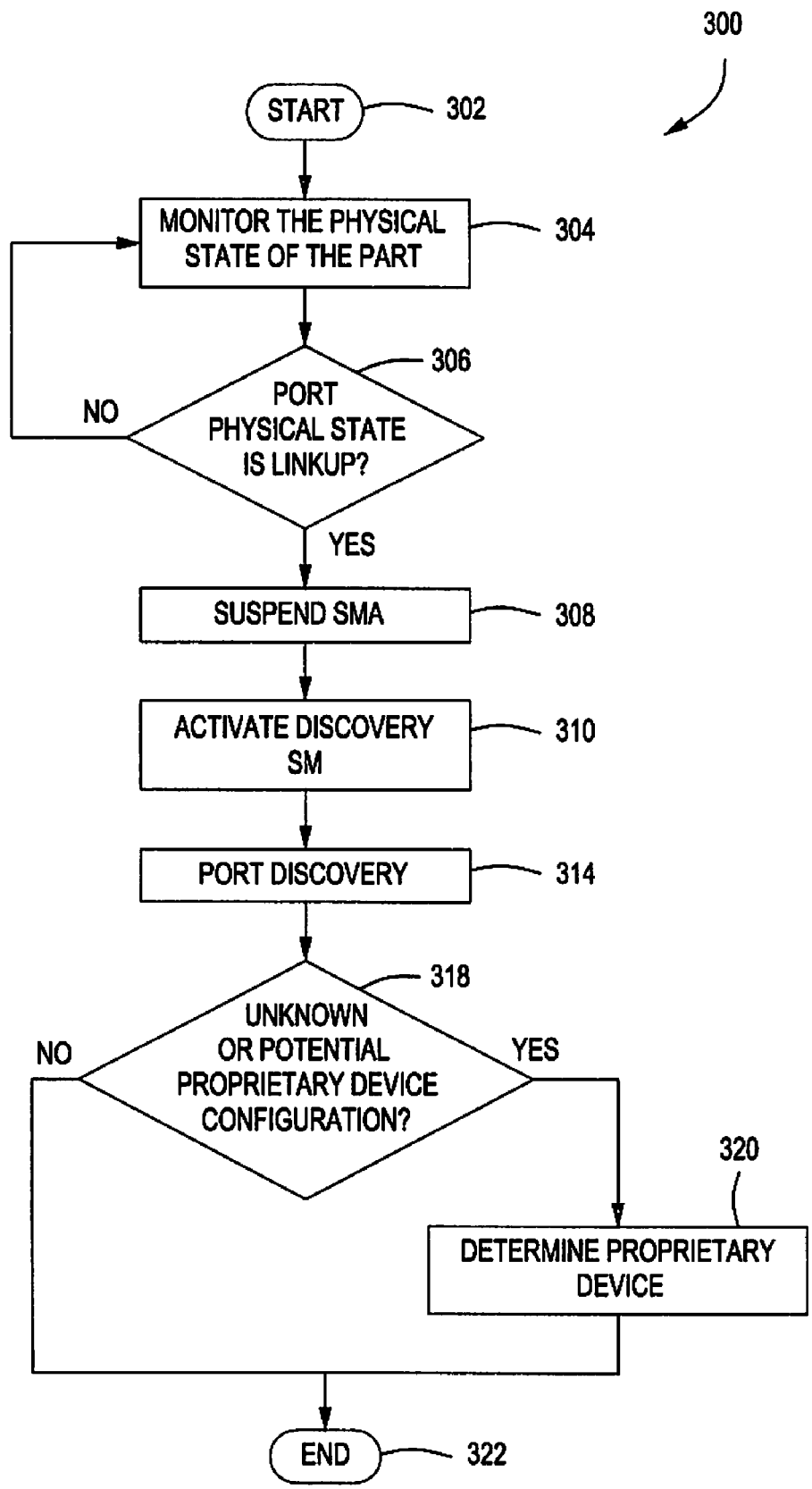
FIG. 4 is a flow diagram of exemplary operations performed in determining the nature of a device connected to a port.

FIG. 4 illustrates a method 300 for determining the nature of a device connected to a port. The method 300 begins at block 302 and proceeds to block 304 where, the physical states of the port are monitored. When it is determined, at block 306, that the physical state of a port changes from LinkDown to LinkUp, a subnet management agent (SMA) for that port may be suspended, at block 308, to allow port discovery. Suspending the SMA may, for example, allow received datagrams to be used for determining the type of connection that is present.

When the SMA is suspended at block 308, it may give up control of all received management datagram events and notify the connection manager 232 of physical port state events. At this point, the discovery subnet manager (DSM 254) for the port may be activated at block 310.

Port discovery may be initiated at block 314, and is discussed in greater detail below with reference to FIG. 5. The port discovery may return results indicating that the device connected to the port is a wrap plug, a wrap cable, a switch or a recognized proprietary device. The port discovery may also return results that indicate an invalid connection, there is an undetermined connection or there is no connection at all. At block 318 it is determined whether an unknown or potential proprietary device configuration was returned. If an unknown or potential proprietary device configuration was returned, the method 300 proceeds to block 320.

At block 320, proprietary packets may be used to determine if the found device is a known proprietary loop device. Operations for determining if the found device is a known proprietary device will be described in greater detail below, with reference to FIG. 6. If a known device is discovered at block 320, it may be reported and if the device is not identifiable an undetermined state may be returned. In any case, the method 300 may proceed to completion block 322. At completion, the discovery subnet manager may enter an inactive state and allow normal subnet management agent processing.

Any management datagrams that the discovery subnet manager 254 receives while the subnet management agent is suspended may be placed in a special queue. When discovery is compete and before the connection manager 232 returns control to the subnet management agent, the discovery subnet manager 254 may add the queued events to the subnet management agent's main queue of events in such a manner so as to preserve their order. It may also be the case that some subnet management agent events cannot be suspended. Examples of such events include timer events and other events already in progress when the discovery subnet manager 254 is activated. Such events will typically not be affected during "suspend mode," but will be processed up to the point where a received management datagram is expected. As previously stated, when the physical state of a port changes from LinkDown to LinkUp, the discovery subnet manager 254 may initiate port discovery on that port.

Figure 5:
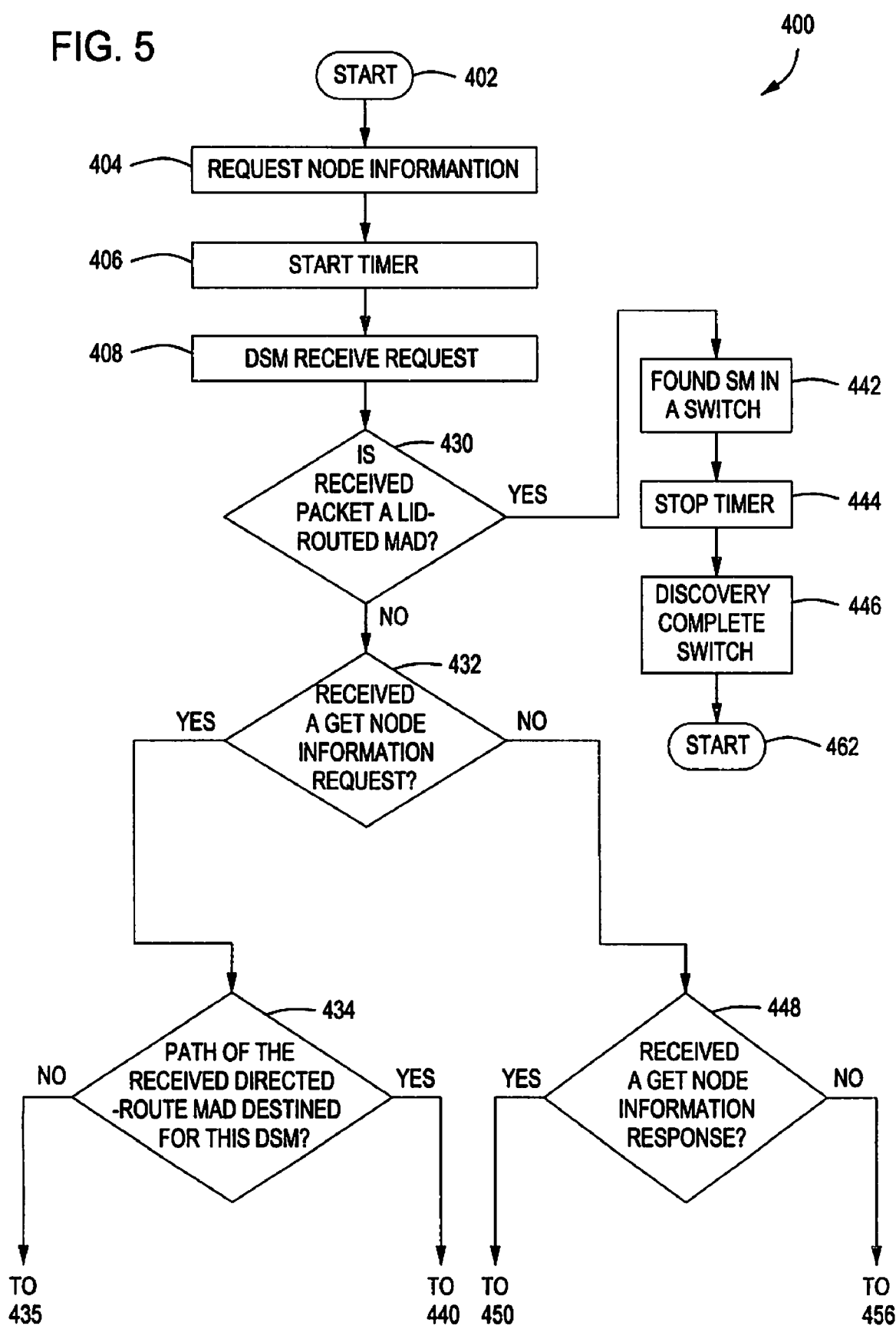
FIG. 5 is a flow diagram of exemplary operations performed by port discovery in determining if the port is connected to a switch or another discovery subnet manager according to an embodiment of the invention.
Figure 5A:
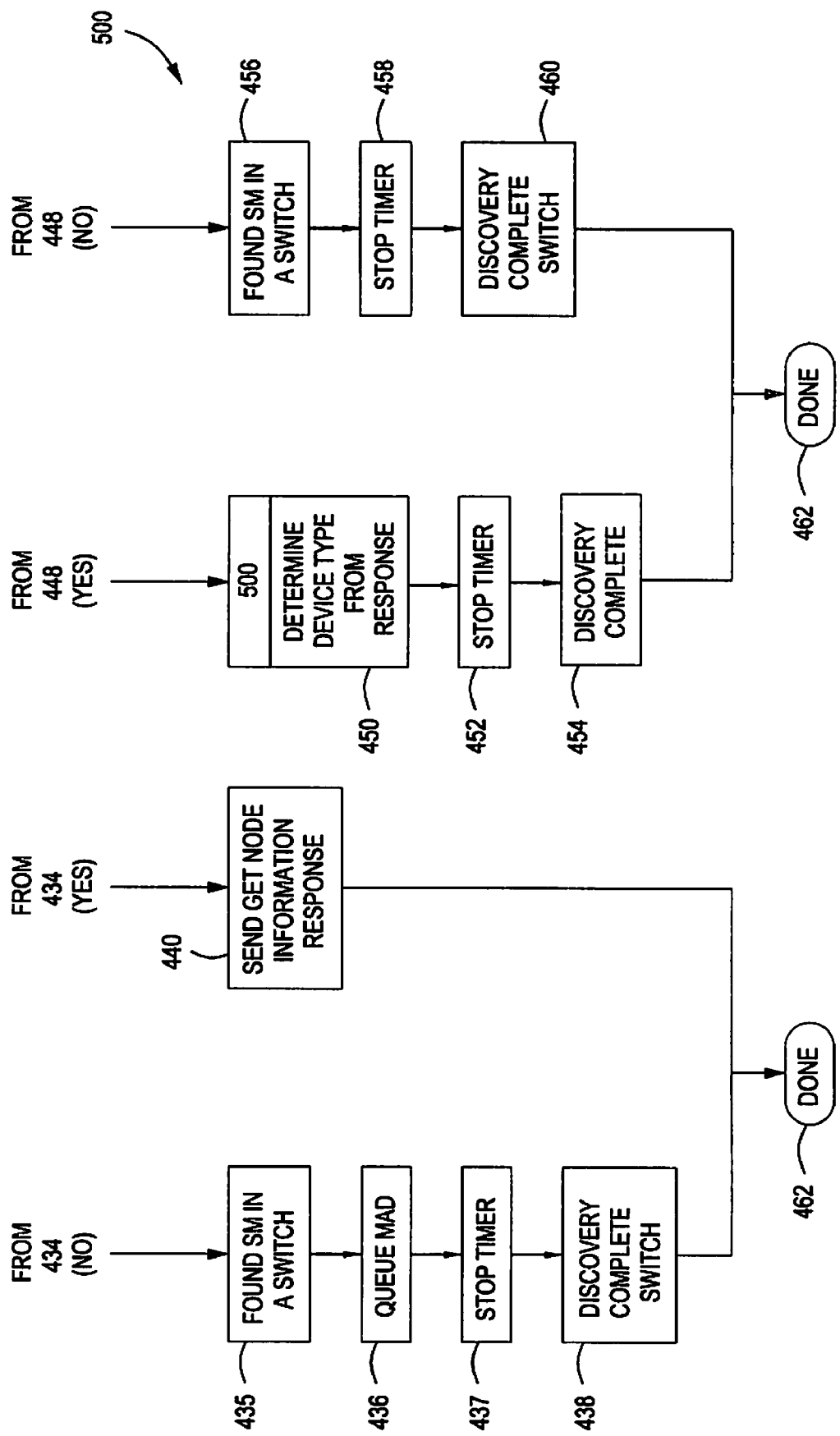

FIG. 5 illustrates exemplary operations 400 for port discovery. The operations 400 begin, at block 402, and proceed to request node information at block 404. A node may be considered a collection of resources with a particular set of associated attributes. The request for node information made at block 404 may be implemented by using a GetNodeInfo command. The GetNodeInfo command may collect detailed state information about idle, busy and defined nodes. Once node information has been requested, a timer may be started at block 406. As responses to the request for node information made at block 404 or other type packets are received, they may be sent to the discovery subnet manager at block 408.

At block 430, a check is performed to see if a received packet is a local identifier (LID) routed management datagram (MAD). If so, because only an SM in a switch will have sent an LID-routed MAD, the operations may proceed to block 442 to confirm a SM in a switch has been found. The timer may be stopped, at step 444, and a state switch to a state indicating a switch has been discovered (Discovery Complete-Switch) may be performed, at step 446. It may be noted that, in the event a switch is discovered, different operations may be performed than a plain Discovery Complete (when a switch is not discovered). Exemplary operations performed to change states in the event that a switch is discovered are described in greater detail below with reference to FIG. 8.

If the received packet is not a LID-routed MAD, the operations may proceed to block 432, to determine if the received packet is a GetNodeInfo request. If so, a determination is made, at block 434, if the path in the received directed-route MAD was destined for this DSM 254 (e.g., for the port on which discovery is taking place). The directed-route portion of the MAD contains a series of port numbers that in total represents a path in the subnet and there may be paths beyond this DSM. If the MAD was destined for this DSM, then this DSM may respond, at block 440, with a GetNodeInfo Response.

It should be noted, however, that discovery is not complete at this point (and the timer should not be stopped), as it is still not known if the device that sent the GetNodeInfo request is another DSM or an SM in a switch. At this point, the timer may be allowed to run down and the GetNodeInfo request may be resent (returning to block 404) or a GetNodeInfo Response may be received (in response to the request sent at block 404) before the timer times out.

Returning to block 434, if the GetNodeInfo Request was not destined for this DSM, the operations may proceed to block 435, where it is confirmed that an SM in a switch was discovered. In other words, only an SM would direct a MAD to an entity other than a DSM. In this case, the MAD may be queued (for later processing), at step 436. The timer may be stopped, at step 437, and a state switch to Discovery Complete-Switch may be performed, at step 438.

Figure 6:
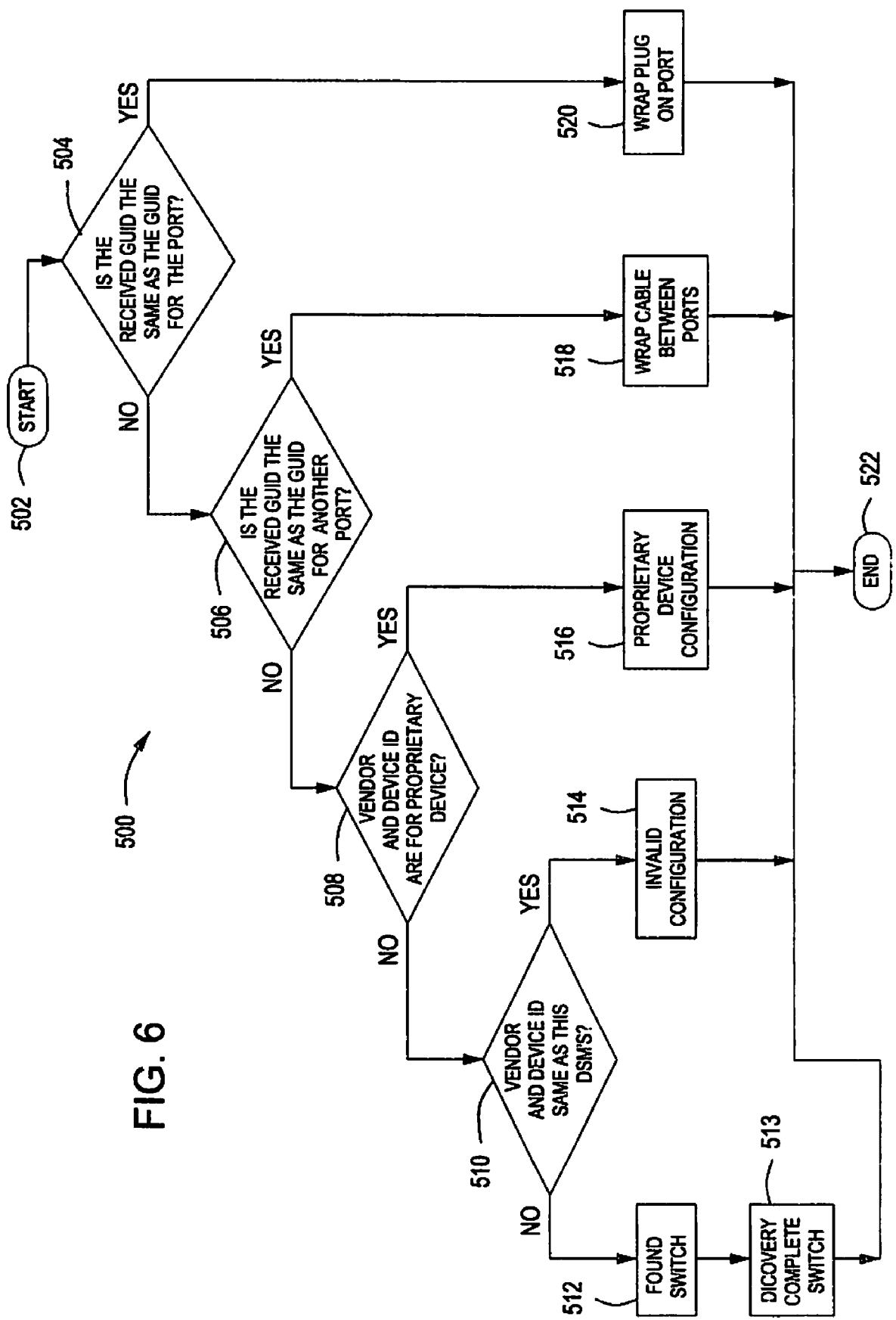
FIG. 6 is a flow diagram of exemplary operations performed in determining what device is connected to a port according to an embodiment of the invention.

Returning to block 432, if a GetNodeInfo Request is not received, operations may proceed to block 448, to determine if a received packet was a GetNodeInfo response. If so, operations may be performed (e.g., as shown in FIG. 6), to determine what type of device is present from the Response. The timer may be stopped at block 452, and a state switch to Discovery Complete may be performed, at step 454.

If the packet was something other than a GetNodeInfo Response, then it can be concluded that the packet was sent by an SM. Accordingly, the operations may proceed to block 456 to confirm a SM in a switch has been found, the timer may be stopped, at step 458, and a state switch to Discovery Complete-Switch may be performed, at step 460.

FIG. 6 illustrates a method 500 for processing received data and identifying devices connected to a port. The method 500 begins at block 502 and proceeds to block 504, where a determination is made as to whether a received globally unique identifier (GUID) is the same as the GUID for the port. If it is determined at block 504 that the GUID is the same as the GUID for the port the method 500 proceeds to block 520 where the connected device is identified as a wrap plug. A wrap plug may be inserted into a port to perform diagnostic testing. Typically, the effect of a wrap plug is to cause the transmitted (output) data to be returned as received (input) data.

If the globally unique identifier (GUID) is not the same as the port, the method 500 may proceed to block 506. At block 506 a determination is made as to whether the GUID is the same as the GUID of another port. If the GUID is the same as another port, it may be determined that there is a wrap cable between the two ports at block 518. Similar to a wrap plug, a wrap cable may be used in diagnostic testing procedures. Typically, the effect of a wrap cable is to cause the transmitted (output) data from one port to be received (input) data at another port.

If the globally unique identifier (GUID) is not the same as that of another port, the method 500 may proceed to block 508. At block 508 it is determined if there is a vendor identification number and a device identification number. If it is determined at block 508 that the vendor and device identification numbers are known to belong to a proprietary device, the method 500 proceeds to block 516. At block 516, a proprietary device is identified as being connected to the port (e.g., an I/O tower or other proprietary system).

If the vendor identification and device identification are not found to be known at block 508, the method proceeds to block 510. At block 510 a determination is made as to whether the vendor device ID is the same as the ID for this DSM performing the discovery. If the vendor and identification numbers are the same, the method 500 proceeds to block 514 and it is determined that an invalid configuration exists for that port. If the vendor and device ID are not the same, the method 500 proceeds to block 512 and it is determined that a switch is connected to the port and a state switch to Discovery Complete-Switch may be performed, at step 513. Once the port configuration has been classified, the method 500 concludes at block 522.

Figure 7:
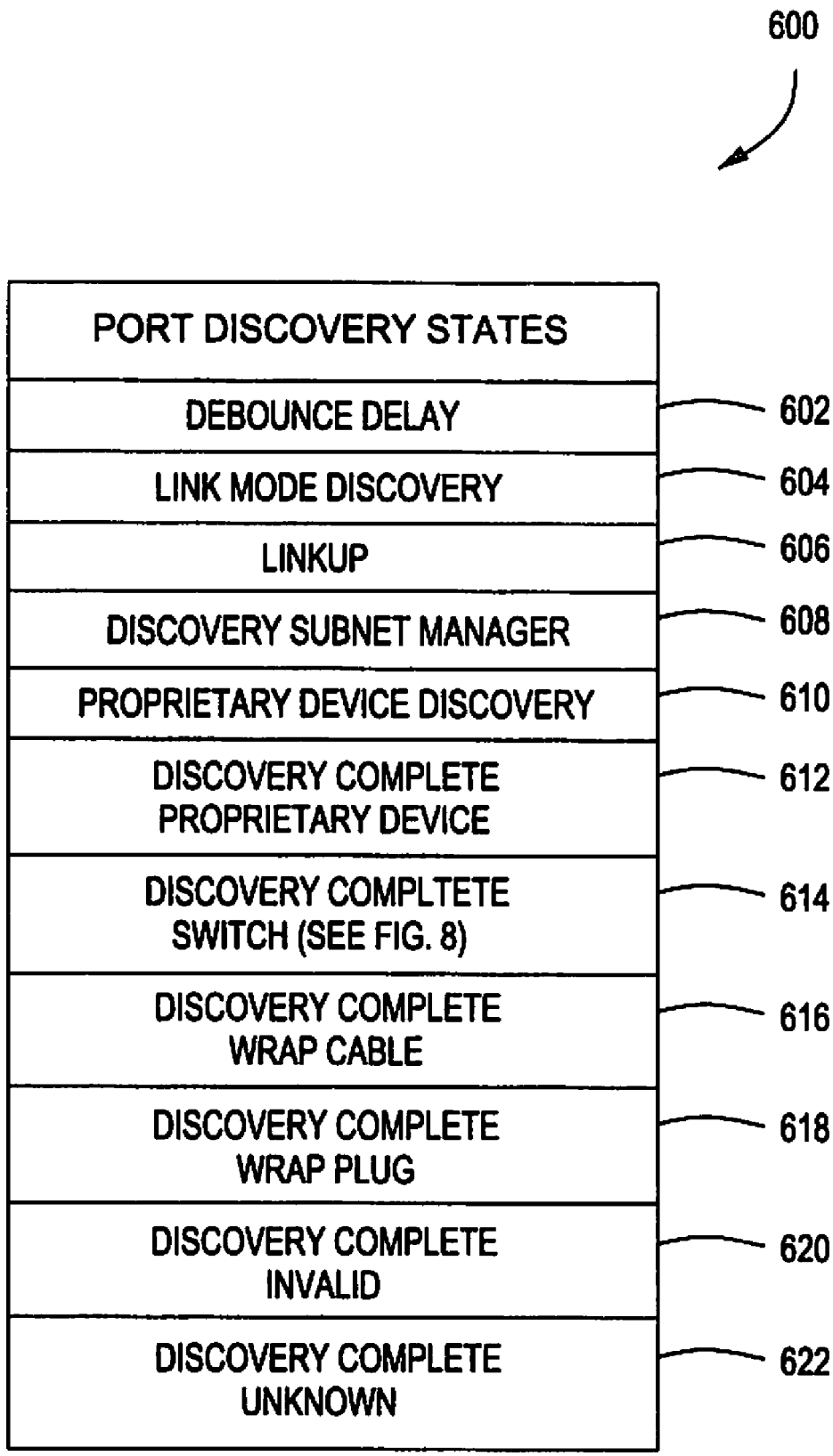
FIG. 7 is an illustration of port discovery states according to an embodiment of the invention.

In general, the port discovery may be in one of the states illustrated in FIG. 7. When a change in the state of a port occurs, the change may not be smooth and continuous. As a result, a condition known as "bounce" may occur. Errors may occur if an action is taken as a result of this bounce. Therefore, the port discovery may be in a debounce delay state 602. In the debounce delay state 602 the port discovery may wait for the port physical state to quiesce before entering link mode discovery state 604.

In the link mode discovery state 604, the port discovery may attempt to discover which electrical characteristics, InfiniBand compliant or non-InfiniBand compliant, will result in a LinkUp port physical state. A LinkUp state 606 may be entered when the port physical state goes to LinkUp. After LinkUp the discovery subnet manager may be started and port discovery may enter a discovery subnet manager state 608. In discovery subnet manager state 608, subnet management packets may be used to discover and evaluate a device on the port.

The discovery subnet manager may return results indicating that a proprietary or unknown device is attached to the port. In such a situation port discovery may enter a Proprietary Device Discovery state 610. Port discovery may also enter a Proprietary Device Discovery state 610 when port discovery for other ports return the same result. In this state, port discovery may use proprietary packets to determine if the device is a known proprietary loop device.

Once discovery is complete, port discovery may enter one of the discovery complete states 612-622. The discovery state entered is determined by the device type discovered. If a proprietary loop is discovered, port discovery may enter a discovery complete, Discovery Complete Proprietary Device state 612. The discovery complete state entered may also be communicated to the connection manager 232. The connection manager 232 may record the discovery state and implement appropriate management protocols 234. Similarly, if a wrap plug is found, port discovery may enter a discovery complete, wrap plug state 618.

Figure 8:
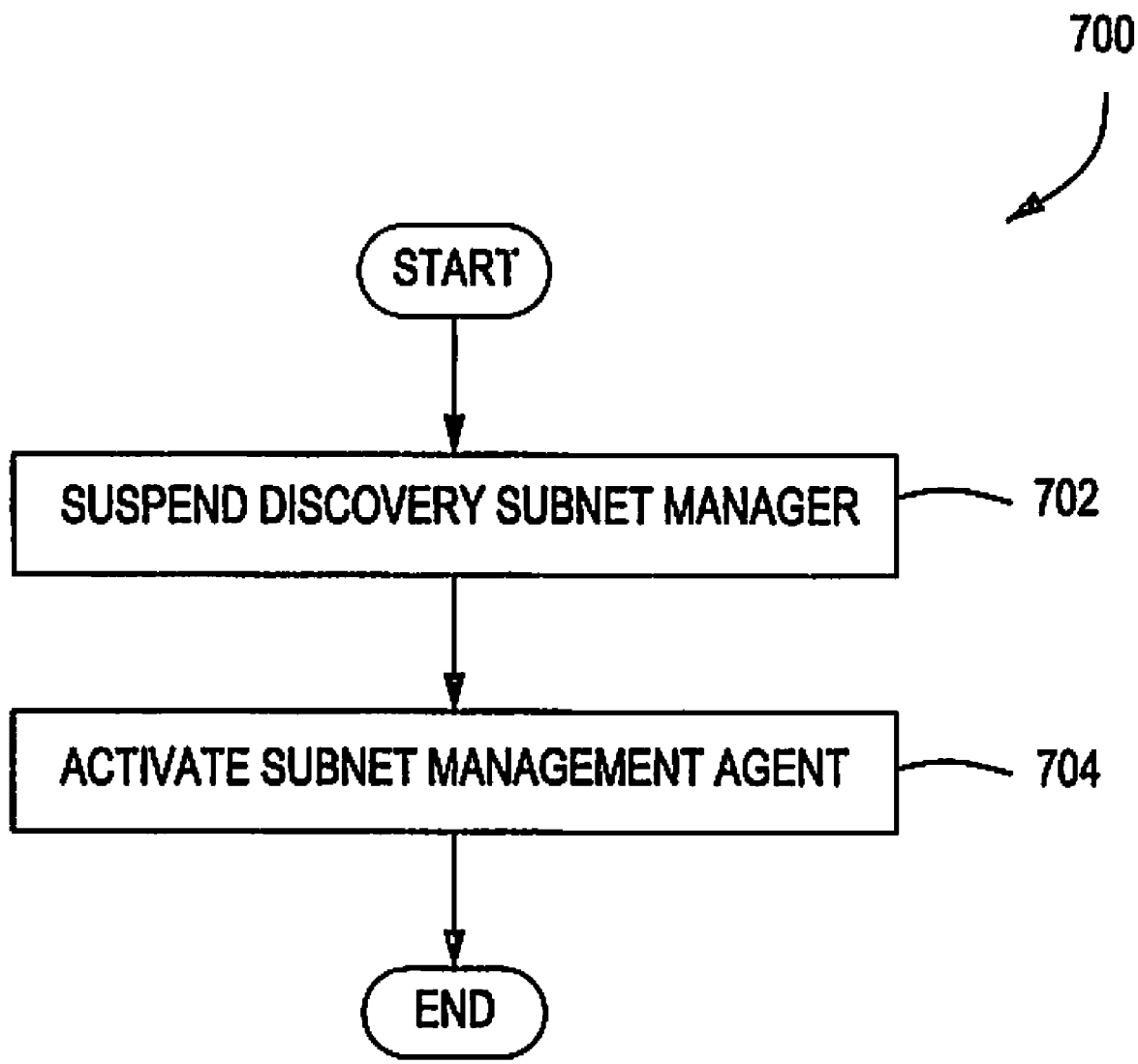
FIG. 8 illustrates exemplary operations for switching to a Discovery Complete state when a switch is discovered.

FIG. 8 illustrates the logical operations 700 that may be performed to implement a state switch to Discovery Complete if an SM in a switch is discovered. As illustrated, Discovery Subnet Manager operations may be suspended, at block 702, and Subnet Management Agent operations may be activated, at block 704. These operations return control of the port (from the DSM) to the SMA.

Connection Management Operations

Figure 9:
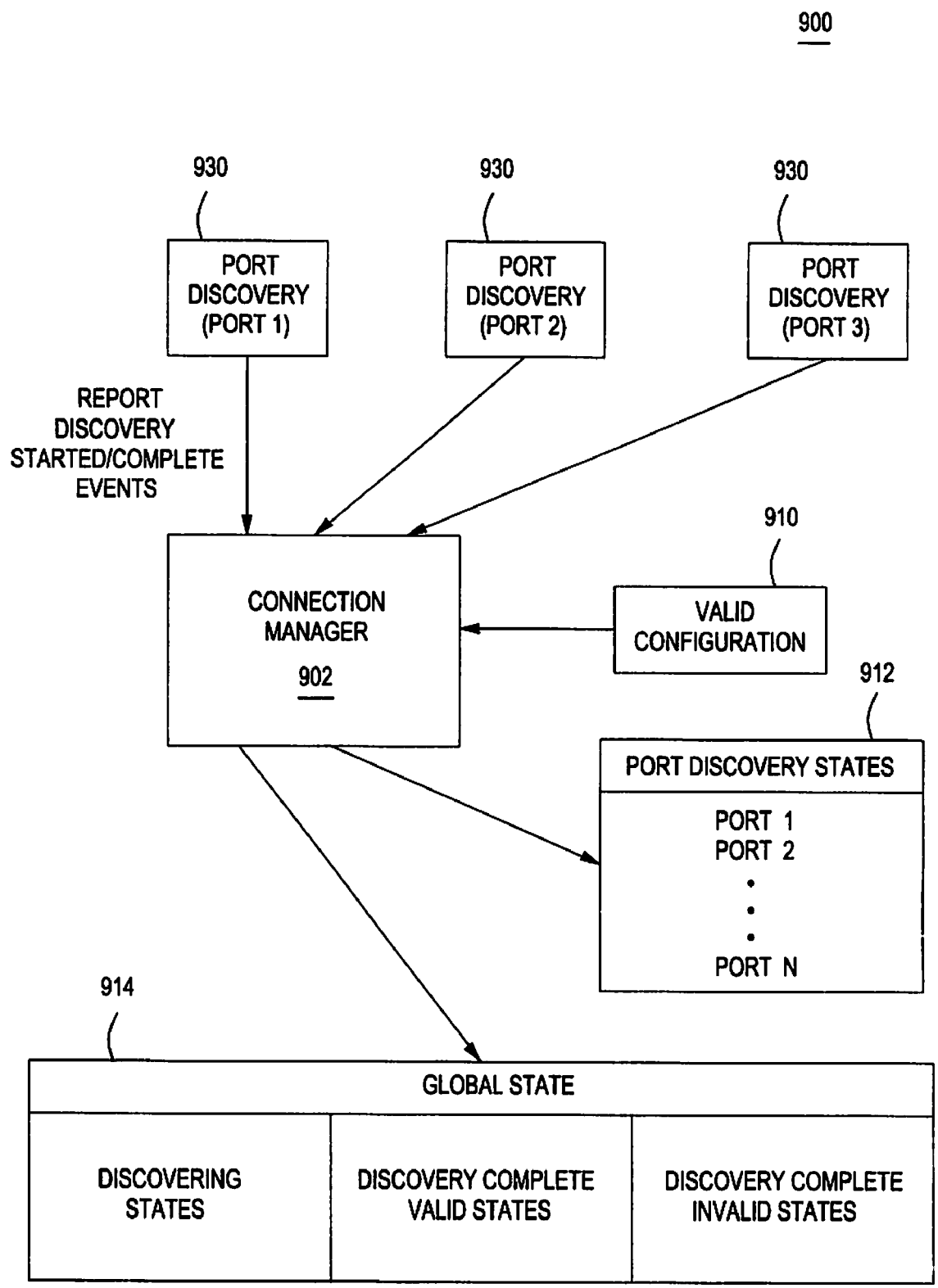
FIG. 9 illustrates an overview of entities involved in connection management according to an embodiment of the invention.

As illustrated in FIG. 9 (and previously discussed with reference to FIG. 2), multiple PortDiscovery entities 930 (e.g., one for each port) may communicate with a Connection Manager 902. For example, the PortDiscovery entities 930 may communicate events to the Connection Manager, such as that operations have been initiated to discover a device on a corresponding port (discoveryStarted) or that such operations are complete (discoveryComplete).

A PortDiscovery entity 930 generally reports a discoveryStarted event to Connection Manager when a physical link falls out of any active state to a Down state. This starts the entire discovery process over again (described above), including physical link training to a PortPhysicalState of LinkUp and the subsequent Discovery Subnet Manager discovery. A PortDiscovery entity 930 generally reports a discoveryComplete event when either the physical link fails to go to a LinkUp state within a reasonable time (e.g., as indicated by expiration of the timer described above) or DSM reports a result after an exchange/receipt of MADs.

The Connection Manager may refer to a ValidConfigurations list 910, which is an object that maintains a system-defined list of what types of devices are allowed in combination with each other on each port in the system. Examples of valid and invalid configurations are described in detail below. The Connection Manager may also maintain a Port Discovery states list 912 that generally represents the Connection Manager's view of the PortDiscovery states returned by the PortDiscovery entity 930 for each port.

The Connection Manager may also maintain a Global State 914 that summarizes the global state or the system, for example, taking into consideration whether valid or invalid device configurations (as determined by object 910) are present. In general, it may be only when the Global State 914 reaches one of the Discovery Complete States (either Valid or Invalid) that the Connection Manager 902 can take action to start proprietary device initialization or stop proprietary device handling.

As an example, some proprietary devices may be configured in loops, with one port of a system connected to another port of a system. In such cases, the Connection Manager may have no way of knowing which ports are in the loop. Thus, the Connection Manager may need the knowledge of all discoveryComplete results for all proprietary devices, and only when the last proprietary device has been discovered, can Connection Manager begin proprietary device initialization. Meanwhile, control may be returned to a subnet manager agent (SMA) immediately for ports discovered to be attached to switches, provided a switch configuration is allowed by ValidConfigurations for that port.

Utilizing a list of valid configurations may allow the management of systems with two or more ports and may provide checking for whether a discoveryComplete result is allowed for a port. One example of valid configurations may be for "proprietary only" configurations. If configured for "proprietary only," valid configurations for a two port system may include the combinations shown in table 1.

TABLE 1

EXEMPLARY PROPRIETARY ONLY CONFIGURATIONS

| PORT1 | PORT2 |
| --- | --- |
| Proprietary Device | Proprietary Device |
| Proprietary Device | Wrap Plug |
| Proprietary Device | Link Down |
| Wrap Cable | Wrap Cable |
| Wrap Plug | Link Down |

Another example may be for a "switch only" configuration, with valid configurations including switches in place of the proprietary devices listed above.

Valid Configurations may be set up in several possible ways, for example, to allow only specific configurations on all ports (as in the above 2-port system example). Valid Configurations may also be set up to allow specific configurations on specific ports. An example in a 3-port system would be to allow ports 1 & 2 to have switches or proprietary configurations, but not a combination, as in the example above, and to allow port 3 to have a switch (or wrap plug) only. Valid Configurations may also be set up to allow specific configurations on a certain number of ports, regardless of port number. An example in a 3-port system would be to allow any two ports to have proprietary configurations only (or wrap plugs or wrap cables) and to allow the third port, regardless of port number, to have a switch only configuration.

In the example of a 2-port system with ValidConfigurations configured for "proprietary," the Connection Manager's 902 Global State 914 may have the following classes of states including Discovering States, Discovery Complete Valid States and Discovery Complete Invalid States.

Discovering States may include the following states: both ports discovering OR one port discovering and the other port any of proprietary, wrap plug, link down, or invalid/unsupported device. DiscoveryComplete Valid States may include the states correspond to the allowed valid configurations for "proprietary only" as shown above. DiscoveryComplete Invalid States for "proprietary only" may include any port is a switch or any port is an invalid/unsupported device. In some cases, a port may be deemed link down (as when a cable is unplugged) if its PortPhysicalState does not go to LinkUp within a reasonable length of time.

Figure 10:
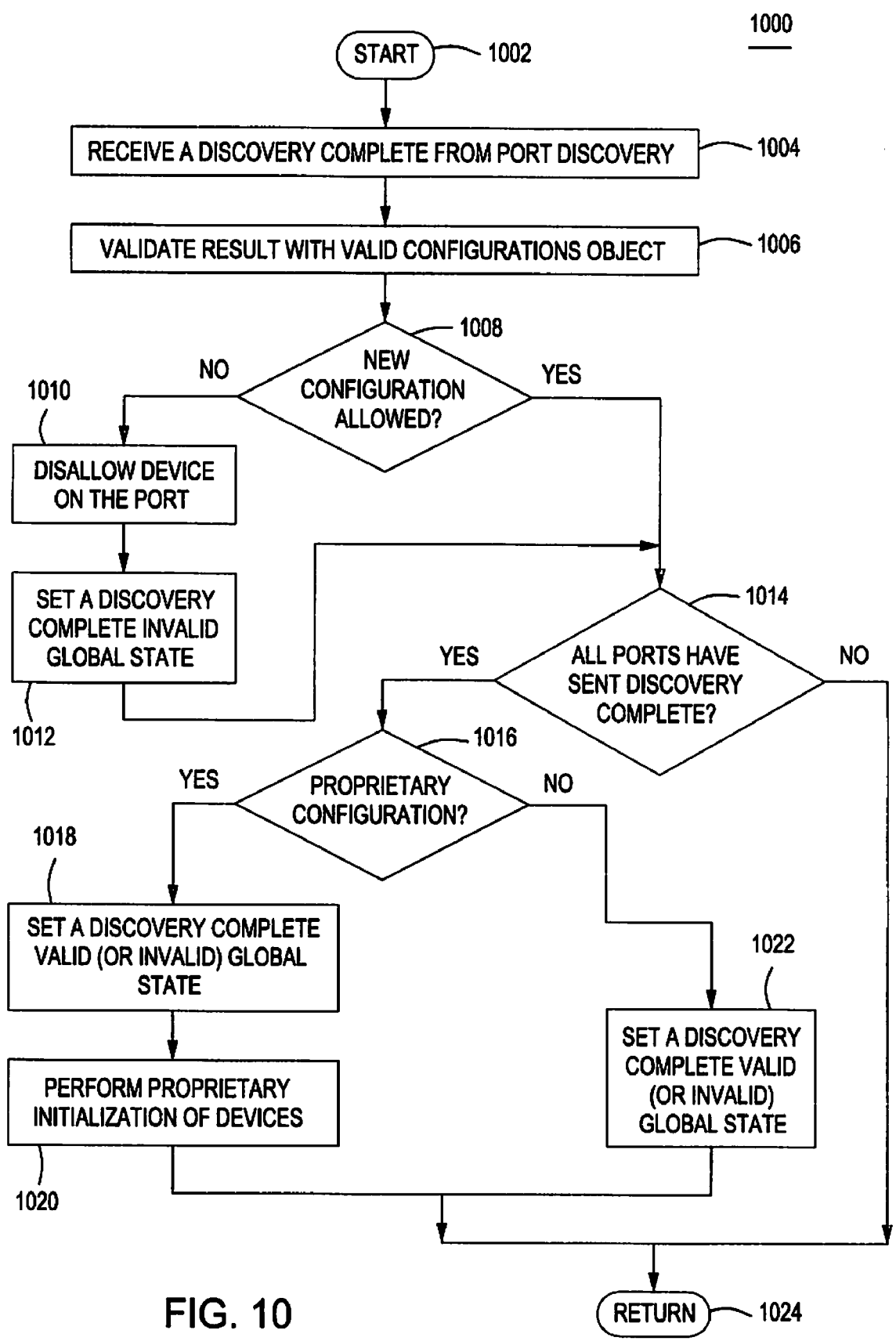
FIG. 10 is a flow diagram of exemplary operations performed when PortDiscovery logic for a port indicates discovery is complete, according to an embodiment of the invention.

FIG. 10 illustrates exemplary operations 1000 that may be performed when the Connection Manager receives notification of a discoveryComplete event. At block 1002, PortDiscovery logic 930 for one of the ports reports a discoveryComplete event to Connection Manager 902. The new state of the port may be saved in Connection Manager's PortDiscoveryStates, at block 1004. At block 1006, the result is validated with the ValidConfigurations object (e.g., the Connection Manager may check to see if the devices connected to the ports constitute a valid configuration). At block 1008, if the result is not allowed for the port in the current configuration DiscoveryCompleteInvalid is set.

At block 1014, a determination is made as to whether all ports have now reported discoveryComplete. If so, at block 1016, a determination is made as to whether there are ports with proprietary configurations. If so, the Connection Manager sets a Global State for DiscoveryCompleteValid (or Invalid), at block 1018 and performs proprietary device initialization for the ports that are proprietary and valid, at block 1020. If there are not ports with proprietary configurations, the Connection Manager sets a different Global State for DiscoveryCompleteValid (or Invalid), at block 1022.

Figure 11:
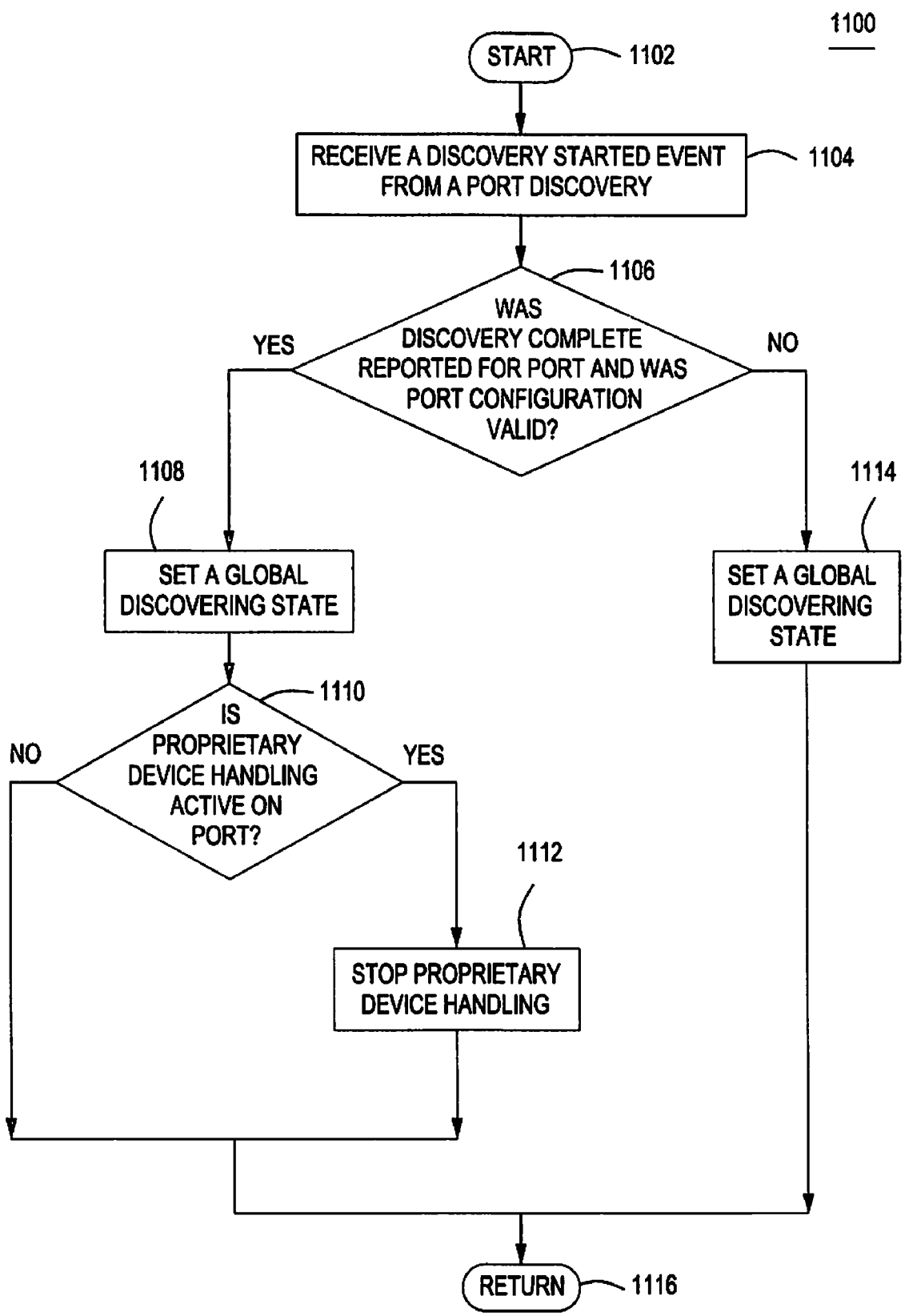
FIG. 11 is a flow diagram of exemplary operations performed when PortDiscovery logic for a port indicates discovery is started, according to an embodiment of the invention.

FIG. 11 illustrates exemplary operations 1100 that may be performed when the Connection Manager receives notification of a discoveryStarted event. The operations begin, at block 1102, when PortDiscovery logic reports a discoveryStarted event, indicating that a port has lost its physical connection and the discovery process begins anew for bringing up the physical link and rediscovering via DSM if a new (or previously known) device is attached. The Connection Manager saves the new state of the port, "Discovering," at block 1104.

At block 1106, a determination is made as to whether discoveryComplete had been reported for the port and if the configuration was valid. If so, the Connection Manager sets a new Global Discovering State, at block 1108. A determination is made, at block 1110, as to whether proprietary device handling is active, and if so, proprietary device handling is halted, at block 1112. If the port is not in a discovery complete valid state, the Connection Manager sets a Global Discovering State, at block 1114.

While the foregoing is directed to embodiments of the present invention, other and further embodiments of the invention may be devised without departing from the basic scope thereof, and the scope thereof is determined by the claims that follow.

What is claimed is:

1. A method of managing one or more devices connected to one or more InfiniBand ports, comprising:

detecting a change in physical state of one of the ports indicating a presence of a device;

in response to detecting the change in physical state, performing discovery operations to determine the type of the present device, wherein the discovery operations include determining whether the device is a proprietary device that is at least partially InfiniBand non-compliant, and communicating with the device using an appropriate protocol for the determined type; and in response to determining the device is InfiniBand non-compliant, suspending an InfiniBand subnet management agent.

2. The method of claim 1, further comprising, in response to determining the device is infiniband non-compliant, assuming control of management datagrams used to control one or more devices that are electrically Infiniband compliant.

3. The method of claim 1, further comprising:
acquiring a list of devices that are allowed use a specified InfiniBand port;
determining if a device connected to the specified port is allowed to use the specified port; and
if the device is not allowed to use the specified port, disabling the port.

4. The method of claim 1, further comprising:
recording changes in the physical state of the port and recording a device identification number for a device that is InfiniBand non-compliant.

5. The method of claim 1, wherein the appropriate protocols allow a device that is InfiniBand non-compliant to communicate with one or more devices that are InfiniBand compliant.

6. The method of claim 2, further comprising:
queuing management datagrams intended for the subnet management agent;
releasing the InfiniBand subnet management agent; and
adding queued management datagrams to a queue of the subnet management agent in such a manner as to preserve the order of the queued management datagrams.

7. The method of claim 2, wherein the one or more devices that are InfiniBand compliant are connected to a different port than the port on which the change in physical state was detected.

8. The method of claim 4 further comprising:
determining whether the device identification number is the same as a specified device identification number; and
disabling the port if the device identification number is not the same as the specified device identification number.

9. A computer-readable storage medium containing a program for managing an InfiniBand port which, when executed, performs operations comprising:
detecting a change in physical state of one of the ports indicating a presence of a device;
in response to detecting the change in physical state, performing discovery operations to determine the type of the present device, wherein the discovery operations include determining whether the device is a proprietary device that is at least partially InfiniBand non-compliant and, if so, performing additional discovery operations to determine the type of device and communicating with the device using an appropriate protocol for the determined type; and
in response to determining the device is InfiniBand non-compliant, suspending an InfiniBand subnet management agent.

10. The computer readable storage medium of claim 9, wherein the operations further comprise, in response to determining the device is InfiniBand non-compliant, assuming control of management datagrams used to control one or more devices that are electrically InfiniBand compliant.

11. The computer-readable storage medium of claim 9, further comprising:
acquiring a list of devices that are allowed use a specified InfiniBand port;
determining if a device connected to the specified port is allowed to use the specified port; and
if the device is not allowed to use the specified port, disabling the port.

12. The computer-readable storage medium of claim 9, further comprising:
recording changes in the physical state of the port and recording a device identification number for a device that is InfiniBand non-compliant.

13. The computer-readable storage medium of claim 10, wherein the operations further comprise:
queuing management datagrams intended for the subnet management agent;
releasing the InfiniBand subnet management agent; and
adding queued management datagrams to a queue of the subnet management agent in such a manner as to preserve the order of the queued management datagrams.

14. The computer-readable storage medium of claim 10, wherein the one or more devices that are electrically InfiniBand compliant are connected to a different port than the port on which the change in physical state was detected.

15. The computer-readable storage medium of claim 12 further comprising:
determining whether the device identification number is the same as a specified device identification number; and
disabling the port if the device identification number is not the same as the specified device identification number.

16. An apparatus, comprising:
one or more InfiniBand ports; and
a port connection manager configured to:
detect a change in physical state of one of the ports indicating a presence of a device,
in response to detecting the change in physical state, performing discovery operations to determine the type of the present device, wherein the discovery operations include determining whether the device is a proprietary device that is at least partially InfiniBand non-compliant and communicating with the device using an appropriate protocol for the determined type, and
in response to determining the device is InfiniBand non-compliant, suspend an InfiniBand subnet management agent.

17. The apparatus of claim 16, wherein the port connection manager is further configured to:
acquire a list of devices that are allowed use a specified InfiniBand port;
determine if a device connected to the specified port is allowed to use the specified port; and
if the device is not allowed to use the specified port, disable the port.

18. The apparatus of claim 16, wherein the port connection manager is further configured to, in response to determining the device is InfiniBand non-compliant, assume control of management datagrams used to control one or more devices that are electrically InfiniBand compliant.

19. The apparatus of claim 18, wherein the port connection manager is further configured to:
queue management datagrams intended for the subnet management agent;
release the InfiniBand subnet management agent; and
add queued management datagrams to a queue of the subnet management agent in such a manner as to preserve the order of the queued management datagrams.

20. The apparatus of claim 18, wherein the one or more devices that are InfiniBand compliant are connected to a different port than the port on which the change in physical state was detected.

* * * * *